United States Patent [19]

Shimizu et al.

[11] Patent Number: 4,922,052
[45] Date of Patent: May 1, 1990

[54] (VINYLPHENYL)PHENYLMETHANE AND METHOD FOR PRODUCING (BENZOYLPHENYL) PROPIONIC ACID

[75] Inventors: Isoo Shimizu; Yasuo Matsumura, both of Yokohama; Yutaka Arai, Tokyo, all of Japan

[73] Assignee: Nippon Petrochemicals Company, Limited, Tokyo, Japan

[21] Appl. No.: 169,853

[22] Filed: Mar. 18, 1988

[30] Foreign Application Priority Data

Mar. 20, 1987 [JP]  Japan .................................. 62-66463

[51] Int. Cl.$^5$ ............................................. C07C 15/12
[52] U.S. Cl. ...................................................... 585/25
[58] Field of Search ........................................... 585/25

[56]  References Cited

U.S. PATENT DOCUMENTS 4,681,980  7/1987  Sato et al. ............................. 585/6.3

*Primary Examiner*—Curtis R. Davis
*Attorney, Agent, or Firm*—Scully, Scott, Murphy & Presser

[57]  ABSTRACT

The invention relates to a new compound of (3-Vinylphenyl)phenylmethane and a method for producing α-(3-benzoylphenyl)propionic acid of ketoprofen without difficulty at low cost and in a high yield. The method comprises the steps of: reacting (3-vinylphenyl)phenylmethane with carbon monoxide and hydrogen, water or lower alcohol in the presence of a transition metal carbonylation catalyst to form α-(3-benzylphenyl)propionic acid derivative, and when the thus obtained compound is an aldehyde, oxidizing methylene group and formyl group of the compound simultaneously or sequentially, or when the obtained compound is an acid or its ester, oxidizing the methylene group of the compound, and if need be, it is followed by hydrolysis.

1 Claim, No Drawings

(VINYLPHENYL)PHENYLMETHANE AND METHOD FOR PRODUCING (BENZOYLPHENYL) PROPIONIC ACID

BACKGROUND OF THE INVENTION

1. Field of the Invention

This invention relates to a new compound of (vinylphenyl)phenylmethane which is represented by the formula (I) and a new method for producing α-(3-benzoylphenyl)propionic acid by using the above compound as an intermediate.

The compound prepared by the method of the present invention is α-(3-benzoylphenyl)propionic acid (tradename: ketoprofen) which is represented by the following formula (III) and which is used as a medicine for the relief of pain, fever and inflammation.

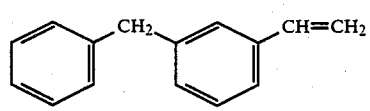
(I)

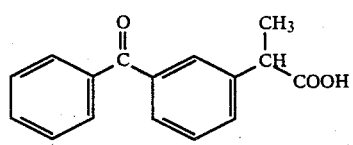
(III)

2. Description of Prior Art

In connection with the ketoprofen, various preparation methods have been hitherto proposed. Among them, typical ones are described briefly in the following.

(1) 3-Methylbenzophenone is subjected to bromination to produce 3-bromomethylbenzophenone, which is then reacted with potassium cyanide to produce 3-cyanomethylbenzophenone. This 3-cyanomethylbenzophenone is then methylated and methyl iodide in the presence of a base. The process is further followed by alkali hydrolysis to obtain ketoprofen (Japanese Laid-Open Patent Publication No. 51-115452).

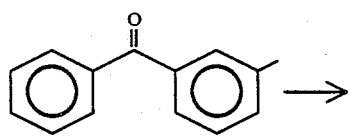

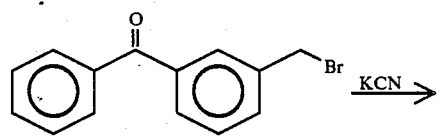

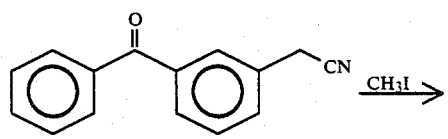

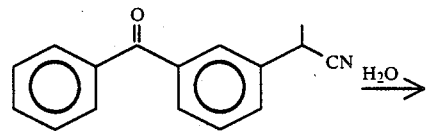

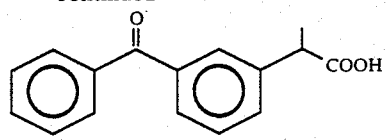

(2) 3-Chlorobenzoic acid is reacted with propionitrile in the presence of a strong base to form α-(3-carboxylphenyl)propionitrile, which is then reacted with thionyl chloride to obtain α-(3-chlorocarbonylphenyl)propionitrile. This compound is further reacted with benzene in the presence of aluminum chloride catalyst (Friedel-Crafts reaction) to obtain 3-(1-cyanoethyl)benzophenone and it is subjected to alkali hydrolysis to produce ketoprofen (Japanese Laid-Open Patent Publication No. 52-8301).

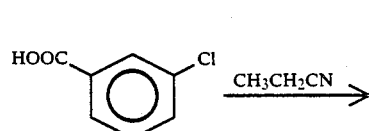

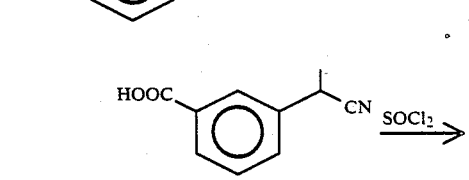

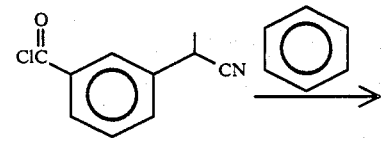

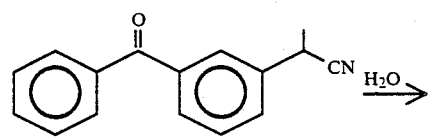

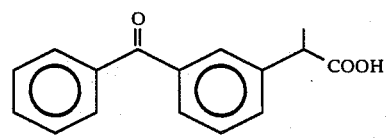

(3) Friedel-Crafts alkylation is carried out with benzophenone and diethyl sulfate in the presence of aluminum chloride to form 3-ethylbenzophenone. It is then subjected to bromination using N-bromosuccinimide to produce 3-(1-bromoethyl)benzophenone, which is then subjected to alkali hydrolysis to obtain 3-(1-hydroxyethyl)benzophenone. This compound is further reacted with carbon monoxide to obtain ketoprofen (Spanish Patent No. 452,500).

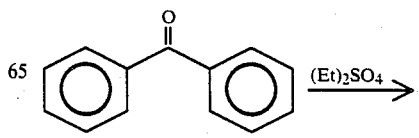

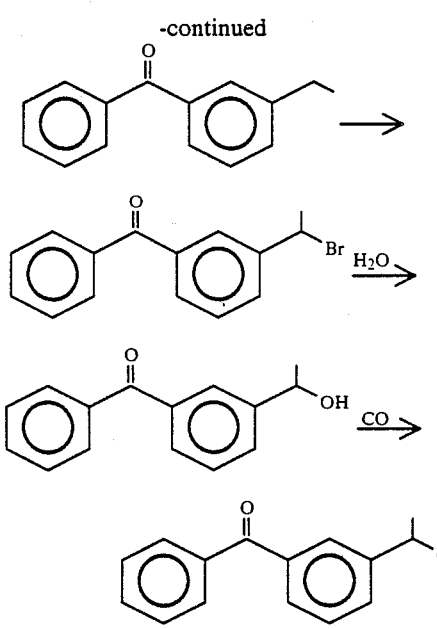

BRIEF SUMMARY OF THE INVENTION

It is, therefore, the object of the present invention to provide a method for synthesizing ketoprofen at low cost and in a high yield.

Another object of the present invention is to provide a new compound which is useful as an intermediate for the process to prepare ketoprofen.

More particularly, the present invention relates to a new compound of (3-vinylphenyl)phenylmethane which is represented by the following formula (I) and a novel method for producing ketoprofen using an intermediate of the above new compound.

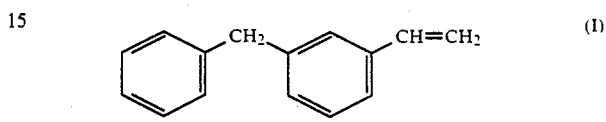

The novel method for producing ketoprofen according to the present invention is schematically illustrated in the following.

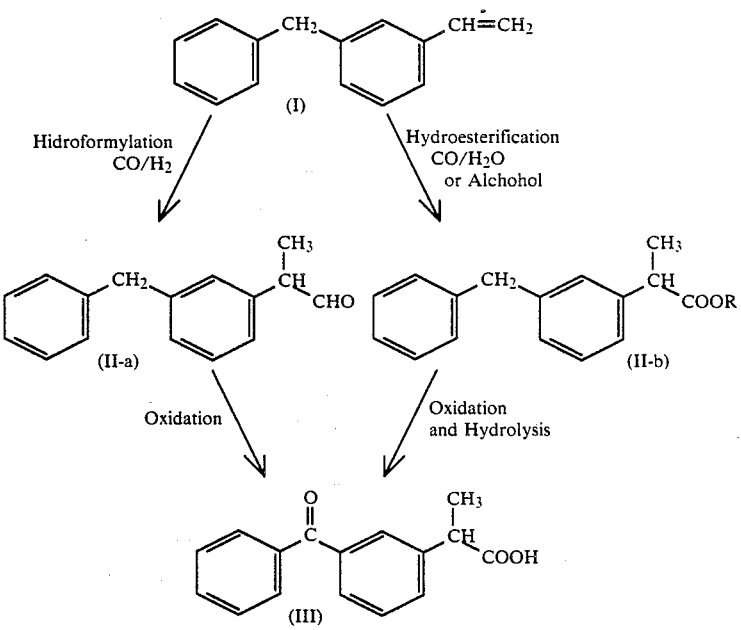

In the case that (3-vinylphenyl)phenylmethane is reacted with hydrogen and carbon monoxide in the presence of a transition metal carbonylation catalyst (hydroformylation), α-(3-benzylphenyl)propionaldehyde (formula II-a, or formula (II) having H as X) which is a precursor of α-(3-benzoylphenyl)propionic acid, can be obtained. Ketoprofen of the formula (III) is obtained by oxidizing the methylene group and the formyl group of α-(3-benzylphenyl)propionaldehyde.

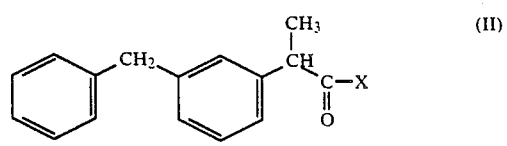

wherein X is H or OR and R is H or a lower alkyl group.

It should be noted, however, that the above method (1) is undesirable as an industrial process because the toxic potassium cyanide is used when 3-cyanomethylbenzophenone is synthesized. The other methods (2) and (3) suffer from the defect of low yield in the synthesis of (3-carboxylphenyl)propionitrile in the former method (2) and in the synthesis of 3-ethylbenzophenone in the latter method (3). Accordingly, they are not satisfactory as industrial production processes. In addition, the method (3) has another disadvantage in that the step to convert ethyl moiety of 3-ethylbenzophenone into propionic acid is difficult and low in yield, which fact is common to processes using 3-ethylbenzophenone.

When (3-vinylphenyl)phenylmethane is reacted with carbon monoxide and water or alcohol in the presence of a transition metal carbonylation catalyst (hydroesterification), α-(3-benzylphenyl)propionic acid or its ester-formula (II-b), or formula (II) having OH or OR as X—which is a precursor of α-(3-benzoylphenyl)propionic acid, can be obtained. Ketoprofen of the formula (III) is obtained by oxidizing, and if necessary hydrolyzing, the methylene group of the above compound.

DETAILED DESCRIPTION OF THE INVENTION

In the first place, the method for producing (3-vinylphenyl)phenylmethane of the foregoing formula (I) is described.

It is possible to prepare the (3-vinylphenyl)phenylmethane by, for example, the following procedure in a high yield.

The method using benzyl chloride as a starting material is described. Benzyl chloride is reacted with a Grignard reagent of 3-vinylphenylmagnesium bromide in the presence of dichlorodiphosphine nickel complex catalyst to obtain (3-vinylphenyl)phenylmethane. The reaction temperature using Grignard reagent is in the range of 10° to 80° C. and the use quantity of Grignard reagent is 1.0 to 1.2 equivalent to 1 mole of benzyl chloride.

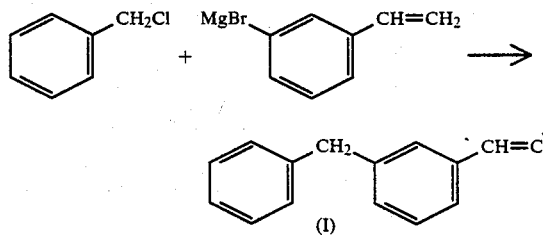

In the following, the hydroesterification and hydroformylation are described. Incidentally, these reactions will be sometimes referred to as "carbonylation", together.

The transition metal catalysts used in the carbonylation are transition metals such as Ni, Co, Fe, Mo, Pd, Pt, Rh, Ir, Ru and Re, preferably the transition metals such as Pd, Rt, Rh, Ir and Ru. As the transition metals, those having oxidation numbers from 0 to the highest numbers can be used. The complex catalysts having ligands of halogen atom trivalent phosphorus compound, π-allyl group, amine, nitrile, oxime, olefin, hydrogen or carbon monoxide can be preferably used.

The transition metal complex catalysts are exemplified by bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine acetate complex, bistriphenylphosphine dinitrate complex, bistriphenylphosphine sulfate complex, tetrakistriphenylphosphine complex; and complexes in which a part of ligands are carbon monoxide such as chlorocarbonyl bistriphenylphosphine complex, hydridocarbonyl tristriphenylphosphine complex, bischlorotetracarbonyl complex and dicarbonyl acetylacetonate complex.

Furthermore, the compounds which produce the above metal complexes in the reaction system can also be used. That is, phosphine, nitrile, allyl compound, amine, oxime, olefin or carbon monoxide which is able to be the ligands to the oxides, sulfates or chlorides of the above transition metals, are simultaneously added into the reaction system.

The above phosphines to be the ligands are exemplified by triphenylphosphine, tritolylphosphine, tributylphosphine, tricyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclodecatriene.

The use of quantity of a complex catalyst or a transition metal compound which can form a complex is 0.0001 to 0.5 mole, preferably 0.001 to 0.1 mole to 1 mole of (3-vinylphenyl)phenylmethane (formula I). When the compound which forms a complex is used, the addition quantity of the compound to form ligands is 0.8 to 10 moles, preferably 1 to 4 moles, to 1 mole of the compound to form a complex.

Furthermore, for the purpose of improving the rate of reaction, it is possible to add inorganic halides such as hydrogen chloride and boron trifluoride, or organic iodide such as methyl iodide.

When these halides are added, the quantities of them are 0.1 to 30 moles, preferably 1 to 15 moles, as halogen atoms to 1 mole of the complex catalyst or the compound to form a complex. Even though the catalytic effect depends upon the kind of catalyst, when the addition quantity is less than 0.1 mole, the effect of the addition cannot be expected sometimes. If the addition quantity exceeds 30 times by moles, not only the catalytic activity is lowered but also halogen atoms are added to the double bonds of (3-vinylphenyl)phenylmethane which fact is a bar to the intended reaction.

The carbonylation is carried out at a temperature in the range of 40° to 150° C., preferably 55° to 130° C. When the reaction temperature is below 40° C., the rate of reaction is very low which is not acceptable in industrial processes. On the other hand, when the reaction temperature is above 150° C., it is not desirable because side reactions of polymerization and addition of hydrogen or alcohol and decomposition of complex catalyst are caused to occur.

When the reaction pressure is not lower than 5 kg/cm², it can be selected arbitrary. When the reaction pressure is lower than 5 kg/cm², the rate of reaction is very low, which cannot be adopted practically. When the reaction pressure is higher, it is desirable because the reaction proceeds faster. However, an excessively high pressure necessitates very high pressure resistance for reaction vessels, so that there is naturally a limit in view of the designing of reaction equipment. Accordingly, it is sufficient that the pressure is lower than 700 kg/cm² in a practical view point.

The hydroformylation reaction to use carbon monoxide together with hydrogen is continued until the lowering of pressure owing to the absorption of the mixed gas of carbon monoxide and hydrogen, is not observed. The reaction time of 4 to 20 hours is generally sufficient.

The carbon monoxide and hydrogen that are necessary for the reaction can be fed either separately or by mixing them in advance. The molar ratio of carbon monoxide and hydrogen to be fed into the reaction system can be selected arbitary. In this hydroformylation, carbon monoxide and hydrogen are consumed or absorbed accurately at a molar ratio of 1:1. Accordingly, because a component which is supplied in excess remains unreacted, the reaction can be made to proceed again if another component is supplied at the time when the lowering of pressure decrease is observed. Even though it depends upon the size of reaction vessel and the mode of reaction, it is generally most effective that carbon monoxide and hydrogen are fed in a molar ratio of 1:1.

After the hydroformylation, the reaction product is subjected to separation, preferably by distillation under a reduced pressure. Then the catalyst and the aimed product of α-(3-benzylphenyl)propionaldehyde (formula II-a) can be separated quite easily. The recovered complex catalyst can be used again for the next hydroformylation process.

In the following, the oxidation process is described in detail.

In the oxidation of α-(3-benzylphenyl)propionaldehyde (formula II-a) which is obtained in the carbonylation using hydrogen, the methylene group and the formyl group are oxidized. It is possible to oxidize both the methylene group and formyl group simultaneously in one step reaction. Meanwhile, it is also possible to combine two steps in which the methylene group is firstly oxidized and the formyl group is then oxidized. Furthermore, the order of oxidation can be reversed. When the formyl group is oxidized later, after the formyl group is blocked in advance by a conventional method, the oxidation is carried out.

When the methylene group is firstly oxidized, α-(3-benzoylphenyl)propionaldehyde of the formula (V) is obtained as a partially oxidized product. When the formyl group is firstly oxidized, α-(3-benzylphenyl)propionic acid of the formula (IV) is obtained also as a partially oxidized product.

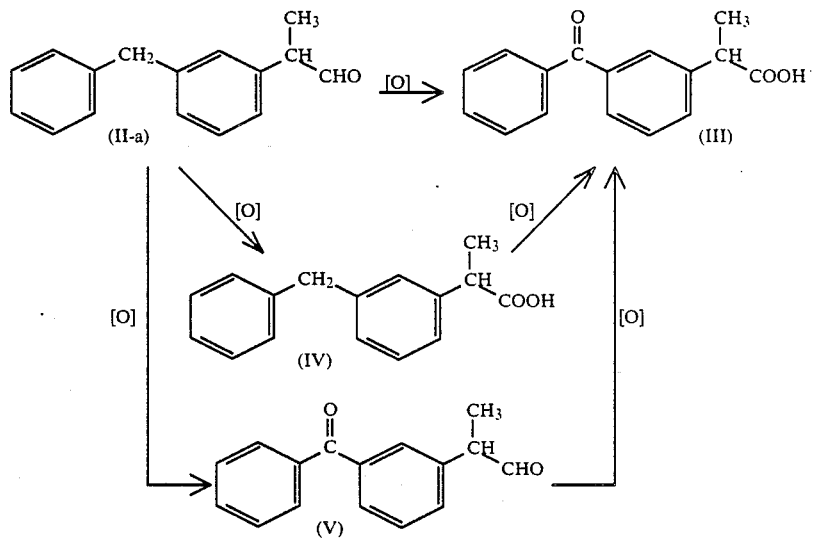

In the hydroesterification using carbon monoxide together with water or alcohol, when (3-vinylphenyl)-phenylmethane of the formula (I) is reacted in the presence of water, a carboxylic acid of the formula (II-b) in which R a hydrogen atom, is obtained. Meanwhile, if the compound is reacted in the presence of a lower alcohol having an arbitrary alkyl group, an ester of the formula (II-b) in which R is an alkyl group of the alcohol, is obtained. For example, a methyl ester is prepared with methyl alcohol.

The alcohols are lower alcohols having 1 to 4 carbon atoms such as methyl alcohol, ethyl alcohol, n-propyl alcohol, isopropyl alcohol, n-butyl alcohol, sec-butyl alcohol, tert-butyl alcohol and isobutyl alcohol. In these alcohols, methyl alcohol is preferable.

After the hydroesterification, the catalyst and the aimed product of α-(3-benzylphenyl)propionic acid or its ester of the formula (II-b) can be easily separated by distillation, preferably under a reduced pressure, the reaction product. The recovered complex catalyst can be used again.

The thus obtained α-(3-benzylphenyl)propionic acid derivative of the reaction product in carbonylation is then oxidized to obtain ketoprofen without difficulty.

It is possible to prepare easily ketoprofen, i.e., α-(3-benzoylphenyl)propionic acid of the formula (III) by oxydation, and if necessary together with hydrolysis, of the α-(3-benzylphenyl)propionic acid or its ester of the formula (II-b) which was obtained by the hydroesterification using water or alcohol. When an ester is obtained by the hydroesterification, it is also possible to hydrolyze the ester into α-(3-benzylphenyl)propionic acid before the oxidation, and it is then oxidized.

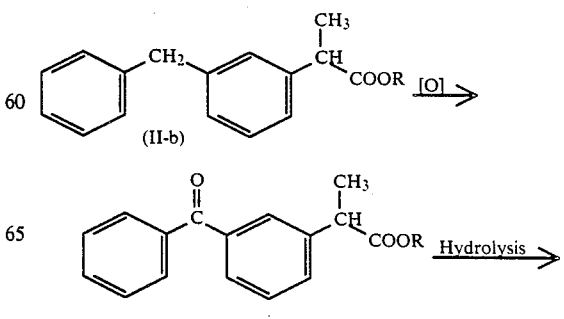

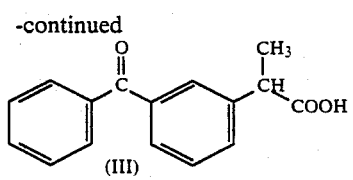

(III)

As the above oxidation method, for example, there are an oxidation method with molecular oxygen in the presence of an oxidation catalyst and another oxidation method using an oxidizing agent such as permanganate, manganese dioxide, chromate, bichromate, lead tetraacetate, periodate, ruthenium tetraoxide, osmium tetraoxide, hydrogen peroxide, selenium dioxide, ozone, and a mixture of them.

The necessary quantity of the oxidizing agent such as permanganates to be added is at least 1 equivalent, preferably more than 1.5 equivalent, to the raw material. There is not especially the upper limit of the use quantity, however, the quantity of more than 10 equivalents is not desirable because it is only uneconomical. The temperature of oxidation using the oxidizing agent is 0° to 200° C. and preferably 30° to 150° C. The reaction cannot proceed at temperatures below 0° C., while by-products are formed and the selectivity to the aimed product is seriously lowered at temperatures below 200° C., both of which are not desirable.

The catalyst used for the oxidation with molecular oxygen are exemplified by the salts of metals selected from the groups VI-B, VII-B and VIII of the periodic table such as chromium, manganese, tungsten, molybdenum, platinum, palladium, cobalt, nickel, iron, rhodium, and ruthenium, or their mixtures. Among them, the salts of cobalt, iron, manganese, and chromium are preferable. As the salts of three metals, naphthenates are preferable. The suitable quantity of a catalyst to be used is 0.05 to 10% by weight to the weight of raw material. As the molecular oxygen, pure oxygen or the air can be used. Furthermore, it is possible to supply the reaction system with a mixture of pure oxygen and other inert gases.

The reaction temperature in the oxidation using molecular oxygen is 30° to 250° C., and preferably 50° to 200° C. In the case that the reaction temperature is lower than 30° C., the rate of reaction is very low, and in the case that the reaction temperature exceeds 250° C., the selectivity to the aimed product is seriously lowered, both of which are not desirable.

In order to improve the contact efficiency of starting materials with an oxidizing agent, a solvent can be used. Such a solvent is exemplified by water, acetone, alcohols such as tert-butyl alcohol, glacial acetic acid, acetic acid, isooctane, benzene, chloroform, and pyridine. They are used singly or as a mixture of them.

After the oxidation, the oxidizing agent or the oxidation catalyst is separated by, for example, filtration, or the reaction mixture is extracted with an organic solvent such as benzene, ethyl acetate or chloroform. After that, highly pure ketoprofen, i.e., α-(3-benzoylphenyl)propionic acid is obtained by the conventional separation method of distillation, recrystallization or the combination thereof. In the case that the oxidation product is an ester, it is hydrolyzed and then refined by conventional methods to obtain easily highly pure α-(3-benzoylphenyl)propionic acid.

As described above, it is possible to prepare easily ketoprofen at low cost and in a high yield by way of the novel intermediate, (3vinylphenyl)phenylmethane that is proposed in the present invention.

Especially, the above intermediate according to the present invention has two benzyl carbon atoms in the structure. That is, the one has two phenyl groups on both sides, the other has one phenyl group on one side. The former benzyl carbon atom is much more susceptible to oxidation than the latter. Moreover, even if this benzyl carbon atom (the former) is readily responsive to oxidation, it is quite stable with regard to carbonylation which is not always mild. Therefore, even after the carbonylation of the vinyl group on the outside of the molecule, the oxidation of this benzyl carbon atom is done easily and outside benzyl carbon atom near the carbonyl group is not susceptible to the further oxidation at all.

The present invention will be described with reference to examples which by no means limit the present invention.

EXPERIMENT 1

Synthesis of (3-vinylphenyl)phenylmethane (Formula I)

To a 2 liter three-neck flask equipped with a reflux condenser and a stirrer was added 50 ml of tetrahydrofuran which was dried with metallic sodium and 28 g (1.15 mole) of metallic magnesium and it was maintained with starring at room temperature. Then, a solution of 183 g (1.02 mole) of 3-vinylbenzene bromide in 500 ml of dry tetrahydrofuran was added dropwise over 2 hours to the above contents. The reaction temperature was maintained at 80° C. After the dropping of the solution, the stirring was continued for further 1 hour at 80° C. The thus obtained Grignard reagent solution was added dropwise over 2 hours to the solution of 171 g (1.0 mole) of benzyl bromide and 5.5 g of NiCl$_2$(Ph$_2$P(CH)$_3$PPh$_2$) in 500 ml of dry ether Stirring was continued for further 1 hour at 35° C. This reaction mixture was poured into iced water and an oily layer was separated. Ether and tetrahydrofuran were evaporated off under reduced pressure to obtain (3-vinylphenyl)phenylmethane of the formula (I) in a yield of 60%.

The analytical data of the reaction product are as follows:

Boiling Point: 108.5–110.5° C./0.5–1 mmHg
IR: (Neat) cm$^{-1}$

| 3040, | 2930, | 1635, | 1600, | 1500, | 1460, |
|---|---|---|---|---|---|
| 995, | 910, | 790, | 710, | 700 | |

$^1$H-NMR: (CCl$_4$, δppm)

| 6.70–7.70 | (9H Multiplet) |
|---|---|
| 6.30–6.60 | (1H Quadruplet) |
| 5.40–5.70 | (1H Doublet) |
| 5.00–5.15 | (1H Doublet) |
| 3.80 | (2H Singlet) |

Elemental Analysis: (as C$_{15}$H$_{14}$)

| Calculated: | C: 92.78% |
|---|---|
| | H: 7.22% |
| Found: | C: 92.80% |
| | H: 7.20% |

EXPERIMENT 2

Synthesis of α-(3-benzylphenyl)propionaldehyde
(Formula II: X=H)-(1)

To a 500 ml autoclave with a stirrer were added 30 g of (3-vinylphenyl)phenylmethane and 0.3 g of rhodium-hydridocarbonyl tristriphenylphosphine and the contents were heated to a temperature of 60° C. and pressurized to 50 kg/cm$^2$ with an equimolar mixture of hydrogen and carbon monoxide. The reaction was continued until the absorption of the mixed gases owing to the reaction was not observed. After the reaction, it was cooled to room temperature and the remained mixed gases were exhausted. The contents were then placed into a reduced-pressure distillation column and α-(3-benzylphenyl)propionaldehyde (formula II: X=H) of 113°–116° C./0.5–1 mmHg in boiling temperature range was obtained in a yield of 95%. The results of spectrum analysis are as follows:

IR: (Neat) cm$^{-1}$

| 3050, | 2990, | 2840, | 2720, | 1735, |
|---|---|---|---|---|
| 1600, | 1500, | 1450, | 1390, | 1090, |
| 1010, | 780, | 700 | | |

$^1$H-NMR: (CCl$_4$, δppm)

| 9.75 | (1H Singlet) |
|---|---|
| 6.65–7.65 | (9H Multiplet) |
| 2.95–3.50 | (3H Multiplet) |
| 1.35–1.50 | (3H Doublet) |

Elemental Analysis: (as C$_{16}$H$_{16}$O)

| Calculated: | C: 85.72% |
|---|---|
| | H: 7.14% |
| | O: 7.14% |
| Found: | C: 88.70% |
| | H: 7.15% |
| | O: 7.15% |

EXPERIMENT 3

Synthesis of α-(3-benzylphenyl)propionaldehyde
(Formula II: X=H)-(2)

The hydroformylation of (3-vinylphenyl)phenylmethane was carried out in the like manner in Experiment 2 using 0.1 g of rhodium oxide and 0.6 g of triphenylphosphine in place of the rhodiumhydridocarbonyl tristriphenylphosphine. As a result, α-(3-benzylphenyl)-propionaldehyde (formula II: X=H) was obtained in a yield of 90%.

EXPERIMENT 4

Synthesis of Ketoprofen (Simultaneous Oxidation)

A solution 20 g of α-(3-benzylphenyl)propionaldehyde (formula II: X=H) obtained in Experiment 2 in 200 ml of benzene was dispersed in 200 ml of water, to which 4 liter of 1.6% solution of potassium permanganate was added dropwise with stirring. After the dropping, stirring were continued for about 10 hours at room temperature. The mixture was then acidified with concentrated sulfuric acid and was treated with 60 g of sodium sulfite. After that, water was added to the reaction mixture and extraction was carried out with ether. The ether layer was washed with water and it was extracted with 5% aqueous solution of potassium hydroxide. The aqueous layer was then acidified with hydrochloric acid and extracted again with ether. The ether layer was washed with water and dried with anhydrous sodium sulfate. The ether was then evaporated off under reduced pressure. Finally α-(-benzoylphenyl)-propionic acid (ketoprofen) was obtained by re-crystallization from benzene/petroleum ether mixture. The melting point and spectrum data were the same as those of an authentic sample.

EXPERIMENT 5

Synthesis of α-(3-benzylphenyl)propionic acid
(Formula II: X=OR, R=H)

To a 500 ml autoclave were added 40 g of (3-vinylphenyl)phenylmethane (formula I), 75 g of 10% hydrochloric acid aqueous solution, 0.8 g of bistriphenylphosphine dichloropalladium, and 80 ml of benzene as a solvent, and the pressure was raised up to 100 kg/cm$^2$ by carbon monoxide at room temperature. After the temperature was raised to 100° C. by heating, the pressure was raised further to 300 kg/cm$^2$. The reaction was continued until the absorption of carbon monoxide owing to the reaction was ceased.

After the reaction, the reaction mixture was cooled and a benzene layer was separated. It was then extracted three times with 50 ml of 5% aqueous solution of sodium hydroxide. Hydrochloric acid was then added to the sodium hydroxide aqueous solution until the pH became 2, which was followed by extraction with chloroform. The chloroform was removed under reduced pressure to obtain 41 g of of light yellow crude crystals.

With regard to the refined sample made from the crude crystals, the melting point and IR spectrum and NMR spectrum data was coincident with those of references.

EXPERIMENT 6

Synthesis of α-(3-benzoylphenyl)propionic acid
(ketoprofen)-(2)

A solution of 24 g of α-(3-benzylphenyl)propionic acid obtained in Experiment 5 in 200 ml of benzene was dispersed in 200 ml of water, to which 2 liter of 1.6% solution of potassium permanganate was added dropwise with stirring. After the dropping, stirring were continued for about 10 hours at room temperature. The mixture was then acidified with concentrated sulfuric acid and was treated with 30 g of sodium sulfite. After that, water was added to the reaction mixture and extraction was carried out with ether. The ether layer was washed with water and it was extracted with 5% aqueous solution of potassium hydroxide. The aqueous layer was then acidified with hydrochloric acid and extracted again with ether. The ether layer was washed with water and dried with anhydrous sodium sulfate. The ether was then evaporated off under reduced-pressure. Finally, α-(3-benzoylphenyl)propionic acid (ketoprofen) was obtained by re-crystallization from benzene/petroleum either mixture. The melting point and spectrum data were the same as those of an authentic sample.

EXPERIMENT 7

Synthesis of α-(3-benzylphenyl)propionic acid methyl ester (Formula II: X=OR, R=CH$_3$)

A mixture of 40 g of (3-vinylphenyl)phenylmethane (formula I) obtained in Experiment 1, 150 ml of 5% hydrogen chloride solution in methyl alcohol, and 1 g of bistriphenylphosphine dichloropalladium was pressurized up to 300 kg/cm$^2$ with carbon monoxide in an autoclave. After after the temperature was raised to 90° C. by heating, the pressure was raised to 700 kg/cm$^2$ with carbon monoxide. The reaction was continued until the absorption of carbon monoxide owing to the reaction was not observed.

After the reaction, the autoclave was cooled, unreacted gases were exhausted, and 1 of potassium carbonate powder was added to the contents. The contents were then subjected to reduced-pressure distillation to obtain α-(3-benzylphenyl)propionic acid methyl ester (formula II: X=OR, R=CH$_3$) was obtained. The yield was 90% on the basis of (3-vinylphenyl)phenylmethane (formula I).

Analytical data are shown in the following.
Melting Point: 118.2°–120.2° C./0.5–1.0 mmHg
IR: (Neat) cm$^{-1}$

| 3050, | 2985, | 1740, | 1605, | 1500, | 1440, |
|-------|-------|-------|-------|-------|-------|
| 1350, | 1250, | 1200, | 1080, | 1035, | 1005, |
| 790,  | 705   |       |       |       |       |

$^1$H-NMR: (CCl$_4$, δppm)

| 6.40–7.40 | (9H Multiplet) |
|-----------|----------------|
| 3.68      | (2H Singlet)   |
| 3.10–3.65 | (4H Multiplet) |
| 1.32–1.51 | (3H Doublet)   |

Elemental Analysis: (as C$_{17}$H$_{18}$O$_2$)

| Calculated: | C: 80.31% |
|-------------|-----------|
|             | H: 7.09%  |
|             | O: 12.60% |
| Found:      | C: 80.35% |
|             | H: 7.10%  |
|             | O: 12.55% |

EXPERIMENT 8

Synthesis of α-(3-benzoylphenyl)propionic acid (ketoprofen)-(3)

A solution of 25.4 g of α-(3-benzylphenyl)propionic acid methyl ester obtained in Experiment 7 in 200 ml of benzene was dispersed in 200 ml of water, to which 2 liter of 1.6% solution of potassium permanganate was added dropwise with stirring. After the dropping, stirring was continued for about 10 hours at room temperature. The mixture was then acidified with concentrated sulfuric acid and was treated with 30 g of sodium sulfite. After that, water was added to the reaction mixture and extraction was carried out with ether. The ether layer was washed with water and the ether was removed by distillation under reduced pressure. The residue was then subjected to hydrolysis with 5% aqueous solution of potassium hydroxide at refluxing temperature for 3 hours. After cooling, oily contents were washed and extracted with ether and the aqueous layer was acifidied with hydrochloric acid and extracted again with ether. The ether layer was washed with water and dried with anhydrous sodium sulfate. The ether was then evaporated off under reduced-pressure. Finally, α-(3-benzoylphenyl)propionic acid (ketoprofen) was obtained by re-crystallization from benzene/petroleum ether mixture. The melting point and spectrum data were the same as those of an authentic sample.

EXPERIMENT 9

Synthesis of α-(3-benzoylphenyl)propionic acid (ketoprofen)-(4)

α-(3-Benzylphenyl)propionic acid methyl ester which was obtained in Experiment 7 was hydrolyzed in the like manner as in Experiment 8 to obtain α-(3-benzylphenyl)propionic acid. The melting point and spectrum data were coincident with those of the α-(3-benzylphenyl)propionic acid obtained in Experiment 5.

This compound was then oxidized in the like manner as in Experiment 6 to obtain ketoprofen. The melting point and spectrum data were coincident with those of an authentic sample.

EXAMPLE 10

Synthesis of α-(3-benzoylphenyl)propionic acid (ketoprofen)-(5)

To a 300 ml reaction vessel with a stirrer were fed 20 g of α-(3-benzylphenyl)propionaldehyde, 0.05 g of cobalt naphthenate and 100 ml of acetic acid as a solvent, and 150 ml/min of pure oxygen was fed into the vessel for 16 hours at a reaction temperature of 110° C. After the reaction, the solvent was removed by reduced pressure distillation to obtain a solid substance. The solid substance was washed five times with 500 ml of water and it was dissolved in 500 ml of ether and washed three times again with water. After that, the ether was removed by reduced-pressure distillation and the product was finally recrystallized with a benzene/petroleum ether mixture to obtain 12 g of α-(3-benzoylphenyl)propionic acid (ketoprofen). The properties such as melting point and spectrum of the final product were the same as those of an authentic sample.

EXPERIMENT 11

Synthesis of α-(3-benzoylphenyl)propionic acid (keptoprofen)-(6)

Reaction was carried out in the like manner as Example 10 except that 200 ml/min of air dried with silica gel was used in place of the pure oxygen and the temperature of the reaction was 150° C., thereby obtaining 10.3 g of ketoprofen. The properties such as melting point and spectrum of the product were the same as those of an authentic sample.

EXPERIMENT 12

Synthesis of α-(3-benzoylphenyl)propionic acid (ketoprofen)-(7)

To a 300 ml reaction vessel with a stirrer were fed 25 g of α-(3-benzylphenyl)propionic acid obtained in Experiment 5, 0.08 g of cobalt naphthenate and 100 ml of acetic acid as a solvent, and 150 ml/min of pure oxygen was fed into the vessel for 16 hours at a reaction temperature of 120 ° C. After the reaction, the solvent was removed by reduced-pressure distillation to obtain a solid substance. The solid substance was washed five times with 500 ml of water and it was dissolved in 500 ml of ether and washed three times again with water.

After that, the ether was removed by reduced-pressure distillation and the product was finally recrystallized with a benzene/petroleum ether mixture to obtain 13.2 g of α-(3-benzoylphenyl)propionic acid (ketoprofen). The properties such as melting point and spectrum of the final product were the same as those of an authentic sample.

EXPERIMENT 13

Synthesis of α-(3-benzoylphenyl)propionic acid (ketoprofen)-(8)

To a 300 ml reaction vessel with a stirrer were fed 25.4 g of α-(3-benzylphenyl)propionnic acid methyl ester obtained in Experiment 7, 0.03 g of cobalt naphthenate and 100 ml of acetic acid as a solvent, and 150 ml/min of pure oxygen was fed into the vessel for 16 hours at a reaction temperature of 120° C. After the reaction, the solvent was removed by reduced-pressure distillation. After that, water was added to the reaction mixture and extraction was carried out with ether. The ether layer was washed with water and the ether was removed by reduced-pressure distillation. After cooling, oily contents were washed and extracted with ether and the aqueous layer was acidified with hydrochloric acid and extracted again with ether. The ether layer was washed with water and dried with anhydrous sodium sulfate. The ether was then evaporated off under reduced-pressure. Finally, 11 g of α-(3-benzoylphenyl)-propionic acid (ketoprofen) was obtained by re-crystallization from benzene/petroleum ether mixture. The melting point and spectrum data were the same as those of an authentic sample.

What is claimed is:

1. (3-Vinylphenyl)phenylmethane which is represented by the following formula (I):

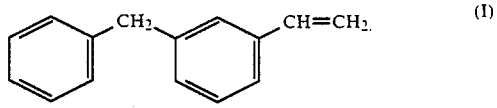

* * * * *